United States Patent [19]

Sandstrom

[11] 4,387,727

[45] Jun. 14, 1983

[54] COAXIAL SERVICE KIT

[75] Inventor: Richard D. Sandstrom, Scandia, Minn.

[73] Assignee: Medtronic, Inc., Minneapolis, Minn.

[21] Appl. No.: 248,735

[22] Filed: Mar. 30, 1981

[51] Int. Cl.³ .............................................. A61N 1/04
[52] U.S. Cl. ............................... 128/784; 128/419 P; 339/177 R
[58] Field of Search ............................... 128/784–786, 128/419 P, 642; 339/177 R, 177 E, 256 S

[56] References Cited

U.S. PATENT DOCUMENTS 3,416,533 12/1968 Fisher et al. ........................ 128/786
3,437,091 4/1969 Jerushalmi et al. ................. 128/786

FOREIGN PATENT DOCUMENTS

WO80/02231 10/1980 PCT Int'l Appl. ................ 128/786

OTHER PUBLICATIONS

"Technical Information–Electrode Pin Replacement Procedure", copyright 1969 by Medtronic, Inc.

Primary Examiner—Lee S. Cohen
Attorney, Agent, or Firm—Reed A. Duthler; John L. Rooney; Joseph F. Breimayer

[57] ABSTRACT

A service kit for splicing body implantable leads having inner and outer coaxially-arranged coil wire conductors insulated from one another. A conductive pin having a distal portion with an outside diameter less than the inside diameter of the inner coil has a barbed tip that is screwed into the inner conductor coil. A shoulder portion of the conductive pin having a larger diameter bears against and retracts the inner coil with respect to the outer coil as the distal portion is screwed into the coil lumen. An insulating sleeve over the shoulder portion assures that the conductive pin does not contact the outer conductor coil. An adaptor housing physically holds the end of the coaxial lead being spliced, the conductive pin and the insulating sleeve. A first set screw through the adapter housing contacts the conductive pin allowing electrical contact thereto. A second set screw through the adapter housing has a sharpened pointed tip by which the outer insulation of the lead is pierced and contact is sustained with the outer conductor coil. The first and second set screws are electrically coupled to coiled wire conductors of the service kit. The entire assembly is fabricated from body compatible materials and suitably sealed against the ingress of body fluids to permit repair of chronically implanted leads.

16 Claims, 5 Drawing Figures

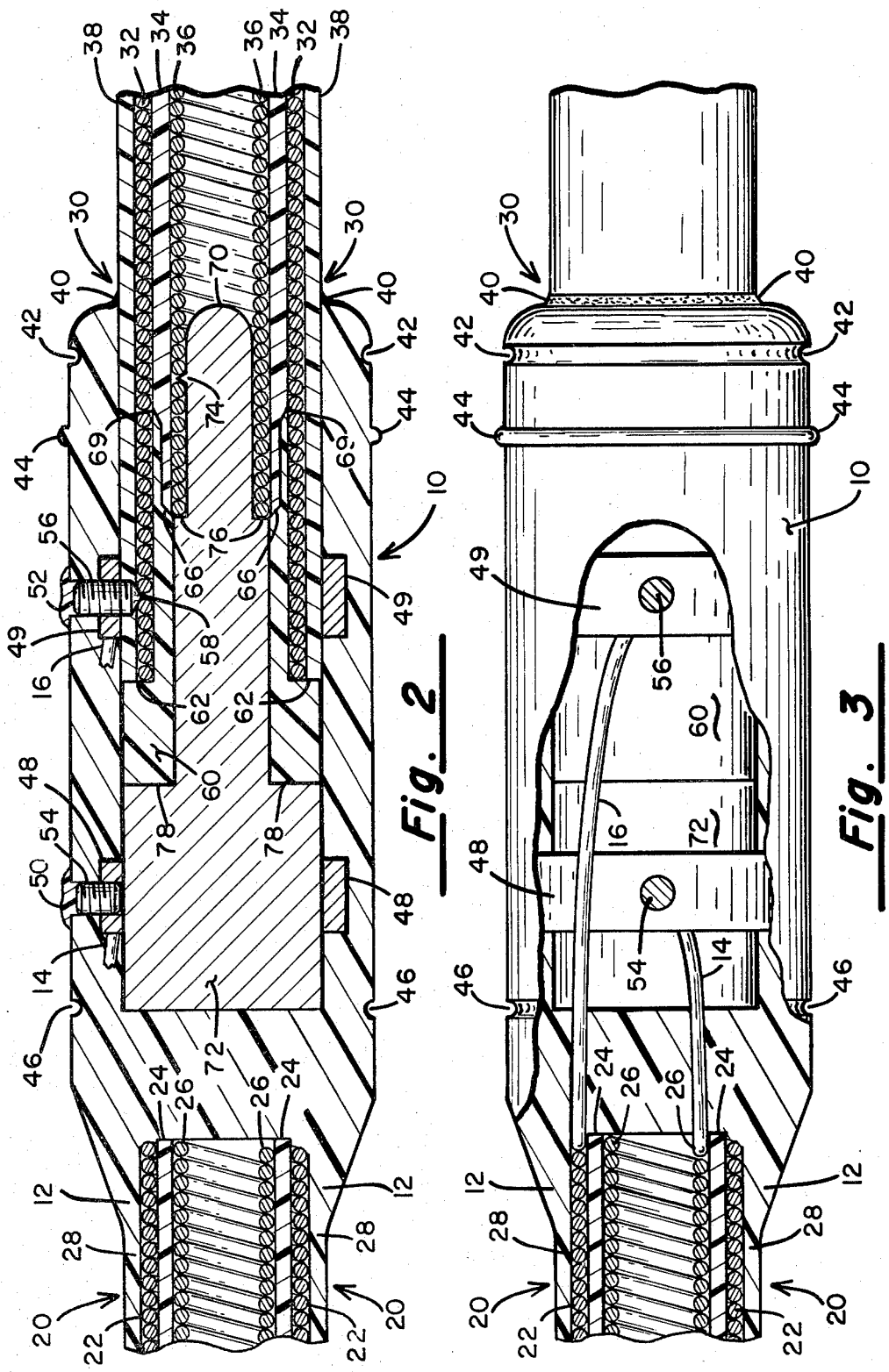

COAXIAL SERVICE KIT

BACKGROUND OF THE INVENTION

1. Field of the Invention

The present invention relates generally to implantable medical devices and more specifically relates to electrical connection means for chronic implantation.

2. Description of the Prior Art

In an effort to assure chronic stability of body implantable electrical leads, various fixation devices have been developed. Whereas it may be safe to remove leads with such fixation devices after a period of time it is often not desirable to do so. Therefore, it is customary to reuse a body implantable lead upon replacement of a pulse generator having a new energy source or having new types of capabilities. Reuse of such body implantable leads oftentimes necessitate repair of damaged areas and replacement of connector terminals. This has occurred very regularly with unipolar leads having a single conductor within the body implantable lead. The assignee of the present invention produces a line of products aimed at splicing such unipolar leads. The model number 5867-X adapters apply to various splicing needs.

The reuse of bipolar leads, on the other hand, has typically resulted in reuse of the lead in unipolar mode in those instances wherein a splice is required. It has been determined to be desirable to be able to splice bipolar leads having coaxial conductors. Any such splicing technique must, of course, be executed within the sterile environment of the operating room since the splice will be chronically implanted. This means that the techniques employed require easy and rapid deployment.

SUMMARY OF THE INVENTION

The present invention permits rapid and reliable splicing of a coaxial body implantable lead. Electrical contact to the inner coil is sustained by a conductive pin which is inserted within the inner conductor coil. A barb at the end of this pin allows the pin to be screwed into the inner conductor coil. In this manner positive and reliable electrical contact is sustained. A set screw within the main housing of the device mechanically and electrically secures the conductive pin.

An insulating sleeve is interposed between the conductive pin and the outer conductor coil of the lead to be spliced. This sleeve insures that the outer coil will not develop a short circuit to either the inner conductor coil or to the electrically common conductive pin. Electrical and mechanical contact is sustained between the main housing and the outer conductor coil by a set screw having a pointed tip. This set screw is screwed through the outer sheath of the body implantable lead and into the outer conductor coil. In this manner, good electrical and mechanical contact is sustained.

The main housing may be permanently attached to a length of body implantable lead as in the case of the preferred embodiment or it may contain a double-ended splicing capability to enable splicing to another portion of the same body implantable lead. A third option places a standard type implantable connector at one end of the main housing and a fourth embodiment uses the main housing as a portion of an implantable pulse generator.

BRIEF DESCRIPTION OF THE DRAWINGS

FIG. 2 is a side sectional view of the apparatus of FIG. 1.

FIG. 3 is a top sectional view showing the method of connection between the set screws and the permanently attached portion of the lead.

DETAILED DESCRIPTION OF THE PREFERRED EMBODIMENT

To be taught is the use of the present invention in a kit for splicing a two-conductor coaxial lead. The main housing of the splicing kit has a permanently attached portion of a two-conductor coaxial lead which itself may be attached to in-line connector terminals (not shown). The main teaching, however, of this disclosure will allow one to readily apply the present invention to other configurations. Examples of related configurations include, for example, a housing with a standard connector receptacle. Also easily accomplished by those of ordinary skill in the art is a two-ended adaptor housing having capability for splicing at either end. Of course, the present invention is also applicable to body implantable leads having more than two conductors.

Figure 1:
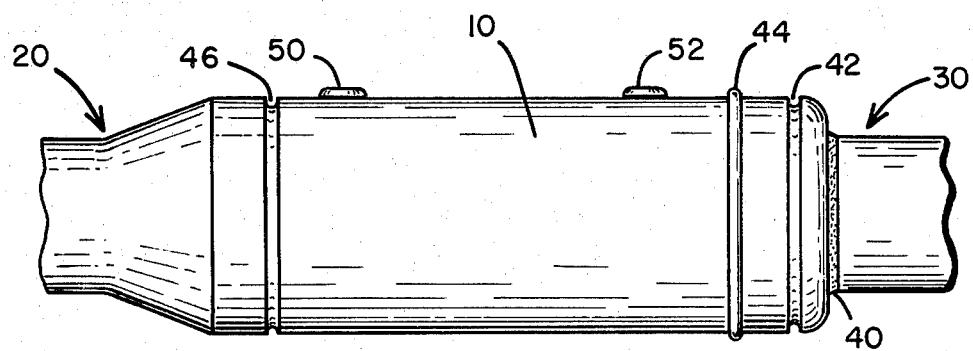
FIG. 1 is a plan view of the coaxial service kit as it appears with the splice complete, ready for chronic implantation.

FIG. 1 is a plan view of the preferred embodiment of the present invention. As shown, main housing 10 is the place at which permanently attached two conductor coaxial body implantable lead 20 is joined with the spliced end of two-conductor coaxial body implantable lead 30. Medical adhesive 40 or other suitable implantable adhesive may be used to facilitate the seal between body implantable lead 30 and main housing 10. Notice that grooves 42 and 46 are available for sutures. Set screw protection 50 and 52 may be provided using medical adhesive to prevent the ingress of body fluids to the apertures containing the set screws for making the permanent attachment. Main housing 10, set screw protections 50 and 52, the outer sheath of two-conductor coaxial body implantable lead 20 and medical adhesive 40 are all of body implantable materials, suitable for chronic implantation.

FIG. 2 is a cross sectinal view of the apparatus shown in FIG. 1. To create a proper splice, body implantable lead 30 must be cut perpendicular to its longitudinal axis at the end to be spliced. The distal end 70 of conducting pin 72 is inserted within the lumen defined by the interior of conducting coil 36. Conducting pin 72 is made of stainless steel or other body compatible conducting material. To facilitate maximum electrical and mechanical coupling, conducting pin 72 has a notch 74 as shown. Notch 74 enables conducting pin 72 to be screwed into conductor coil 36. The shoulder 76 of conducting pin 72 insures that a good mechanical fit is obtained as the conductor coils 36 are compressed together. The conducting pin 72 is screwed into inner conducting coil 36 until conducting coil 36 rests firmly against shoulder 76. As shown, this causes the inner conducting coil 36 to recede from the proximal end of the splice because of the distance between shoulder 76 and shoulder 62. The inner conductor coil 36 and insulating tube 34 are loosely arranged within the outer conductor coil 32 and sheath 38. Consequently, the inner conductor coil 36 and sheath 34 can be compressed and retracted into the lumen of the conductor coil 32.

Before inserting conducting pin 72, insulating sleeve 60 is positioned over conducting pin 72. Insulating sleeve 60 is made of a body compatible rigid insulating material such as urethane. Insulating sleeve 60 must be sufficiently rigid to protect against penetration of pointed set screw 56 (see below). Insulating sleeve 60 is positioned rigidly against conducting pin 72 at shoulder 78. Insulating sleeve 60 is tapered at positions 66 and 69 as shown. This causes a tight fit between the distal end of insulating sleeve 60 and inner insulating sheath 34 as shown. After inserting the insulating sleeve 60 over conducting pin 72 and screwing conducting pin 72 into inner conducting coil 36, electrical contact is established between conducting pin 72 and inner conducting coil 36 with adequate insulation from outer conducting coil 32 as shown. Notice that outer conducting coil 32 becomes lodged firmly against shoulders 62 of insulating sleeve 60. This firm attachment insures adequate mechanical and electrical coupling within the adapter, and causes conducting coil 36 to recede as explained above.

Electrical contact between conducting pin 72 (and thus inner conducting coil 36) is sustained by set screw 54 being screwed into intimate contact with conducting pin 72 as shown. This establishes contact with inner adaptor conductor 14 which is electrically connected to inner coil 26 of permanently attached, body implantable lead 20. This connection is shown in greater detail in FIG. 3 and is discussed below.

Electrical contact with outer conductor coil 32 is sustained by set screw 56. Notice that set screw 56 has pointed tip 58 which is screwed directly into outer conductor coil 32. Pointed tip 58 thus pierces the outer insulation and comes into intimate mechanical and electrical contact with outer conductor coil 32. This piercing is assured since outer conductor coil 32 rests firmly upon insulating sleeve 60, which is in intimate contact with conducting pin 72. Inner adaptor conductor 16 is in contact with set screw 56 which establishes electrical contact with outer conductor coil 22 of permanently attached, body implantable lead 20. Insulating sleeve 60 is sufficiently rigid to prevent piercing by set screw 56 which would cause a short circuit to conducting pin 72.

After installation of set screws 54 and 56, the corresponding aperture may be further sealed by set screw protection 50 and 52 of medical adhesive. This prevents the ingress of body fluids to the interior of main housing 10.

FIG. 3 is a top sectional view showing inner adaptor conductors 14 and 16. Notice that they are placed in intimate contact with set screws 54 and 56, and are connected electrically at the other end with inner conductor coil 26 and outer conductor coil 22 respectively of body implantable lead 20.

Figure 4:
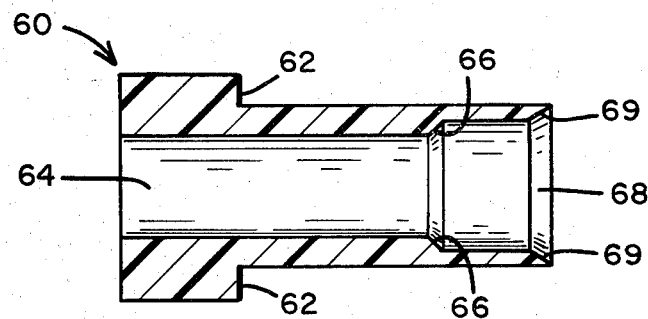
FIG. 4 is a sectional view of the insulating sleeve.

FIG. 4 is a detailed side sectional view of insulating sleeve 60. It is fabricated of a body compatible rigid insulating material such as urethane. It contains a longitudinal lumen 64 which is of sufficient diameter for the insertion of conducting pin 72. Shoulder 62 is to establish secure mechanical contact with the proximal end of outer conductor coil 32 and the outer insulating sheath of body implantable lead 30. The distal end of insulating sleeve 60 is pointed at 69, allowing for the secure mechanical contact between outer conductor coil 32 and inner insulating sheath 34. The pointed distal end creates enlargement 68 of lumen 64 as shown. Within this enlargement will be found inner conductor coil 36 (see also FIG. 2). Inner insulating sheath 34 is enlarged by shoulder 66 as shown. Notice that shoulder 66 is slanted to encourage the maximum travel of inner insulating sheath 34 which insures a tight insulated fit.

Figure 5:
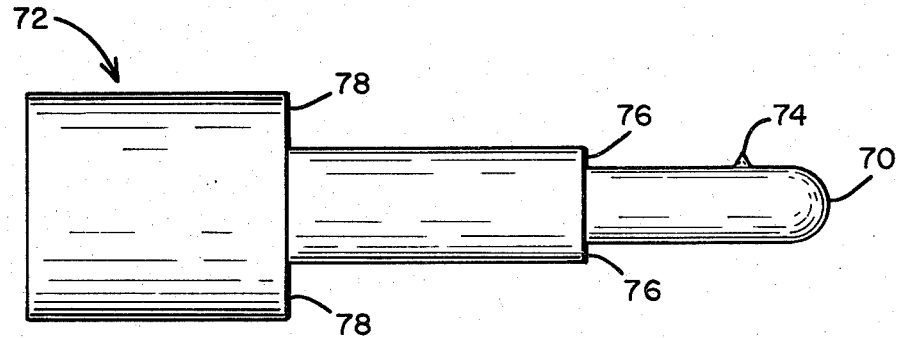
FIG. 5 is a side view of the conducting pin showing the attached barb.

FIG. 5 is a side view of insulating pin 72. Distal portion 70 is of an outside diameter sufficiently small to readily be inserted within inner conducting coil 36. Notch 74 must be of sufficient size to create a radius of curvature which enables conducting pin 72 to be screwed inner conducting coil 36. Shoulder 76 engages inner conducting coil 36 and inner insulating sheath 34.

Shoulder 78 engages insulating sleeve 60 (see also FIG. 2). Conducting pin 72 is made of a body compatible, low electrical resistance material. Stainless steel No. 304 is preferred.

The preceding description provides those of ordinary skill in the art with the opportunity to practice the present invention with configurations different from those taught herein and yet within the scope of the present invention. For example, those of ordinary skill in the art will be readily able to apply the present invention to double-ended splicing of coaxial body implantable leads.

What is claimed is:

1. Apparatus for splicing the cut end of a body implantable lead of the type comprising:
   an outer insulating sheath having a cut end and a lumen open to said cut end;
   an outer conductor coil having a cut end and a lumen open to said cut end, mounted within the lumen of said outer insulating sheath;
   an inner insulating sheath having a cut end and a lumen open to said cut end, mounted within the lumen of said outer conductor coil; and
   an inner conductor coil having a cut end and a lumen open to said cut end, mounted within the lumen of said inner insulating sheath;
   said apparatus comprising:
   a conducting pin for insertion into the lumen of said inner conductor coil;
   insulating sleeve means located coaxial to said conducting pin for preventing said conducting pin from contacting said outer conductor coil;
   first means for electrically coupling to said conducting pin; and
   second means for electrically coupling to said outer conductor coil.

2. Apparatus according to claim 1 wherein said conducting pin has notch means for screwing into said inner conductor coil.

3. Apparatus according to claim 2 further comprising:
   housing means for enclosing said conducting pin, said insulating sleeve means, and for maintaining said first means and said second means in electrical contact with said conducting pin and said outer conductor coil, respectively.

4. Apparatus according to claim 3 further comprising:
   an implantable lead fixedly attached to said housing means having a first conductor electrically coupled to said first means and a second conductor electrically coupled to said second means.

5. Apparatus according to claim 1 or claim 2 or claim 3 or claim 4 wherein said second means is a set screw having a pointed tip.

6. Apparatus according to claim 5 wherein said first means is a set screw.

7. Apparatus according to claims 1 or 2 or 3 or 4 wherein said insulating sleeve means further comprises tubular means for insertion between said outer conductor coil and said inner insulating sheath to accomplish secure mechanical contact between said outer conductor coil and said inner insulating sheath.

8. Apparatus for splicing the cut end of a body implantable lead of the type comprising:
    an outer insulating sheath having a cut end and a lumen open to said cut end;
    an outer conductor coil having a cut end and a lumen open to said cut end mounted within the lumen of said outer insulating sheath;
    an inner insulating sheath having a cut end and a lumen open to said cut end, mounted within the lumen of said outer conductor coil; and
    an inner conductor coil having a cut end and a lumen open to said cut end, mounted within the lumen of said inner insulating sheath;
    said apparatus comprising:
    conductor pin means for contacting and retracting the cut end of said inner conductor coil into the lumen of said outer conductor coil;
    insulating sleeve means having a proximal end and a distal end, located coaxial to said conductor pin means for preventing said conductor pin means from contacting said outer conductor coil;
    housing means for enclosing said conductor pin means, said insulating sleeve means, and the cut end of said outer insulating sheath;
    first means for making electrical contact through said conductor pin means with said inner conductor coil; and
    second means for making electrical contact with said outer conductor coil.

9. Apparatus according to claim 8 wherein said conductor pin means further comprises:
    a distal portion for insertion into the lumen of said inner conductor coil and first shoulder means proximal to said distal portion for abutting the cut end of said inner conductor coil.

10. Apparatus according to claim 9 wherein said insulating sleeve means further comprises:
    second shoulder means for abutting the cut end of said outer conductor coil, proximal to said first shoulder means.

11. Apparatus according to claim 10 wherein said conductor pin means further comprises:
    third shoulder means for abutting the proximal end of said insulating sleeve means, proximal to said second shoulder means.

12. Apparatus according to claim 11 wherein said insulating sleeve means extends between said first and third shoulder means for electrically insulating said outer conductor coil from said conducting pin means.

13. Apparatus according to claim 12 wherein said housing means further comprises:
    bore means for receiving said conductor pin means and the cut ends of said inner and outer conductor coils and wherein said first means is positioned in said housing means overlying said conductor pin means and said second means is positioned in said housing means overlying the cut end of said outer conductor coil when said conductor pin means and the cut ends of said inner and outer conductor coils are received in said bore means.

14. Apparatus according to claim 13 wherein said conductor pin means has notch means for screwing into said inner conductor coil.

15. Apparatus according to claims 8, 9, 10, 11, or 12, wherein said insulating sleeve means further comprises:
    tubular means at the distal end of said insulating sleeve means for insertion between said outer conductor coil and said inner insulating sheath to accomplish secure mechanical contact between said outer conductor coil and said inner insulating sheath.

16. Apparatus according to claim 15 wherein said insulating sleeve means further comprises a shoulder means proximal to said tubular means for abutting the cut end of said inner insulative sheath.

* * * * *

UNITED STATES PATENT AND TRADEMARK OFFICE
CERTIFICATE OF CORRECTION

PATENT NO. : 4,387,727
DATED : June 14, 1983
INVENTOR(S) : Richard D. Sandstrom

It is certified that error appears in the above-identified patent and that said Letters Patent are hereby corrected as shown below:

Column 4,
line 3, "enlarged" should be --engaged--.

*Signed and Sealed this*

*Twenty-seventh* Day of *September 1983*

[SEAL]

Attest:

GERALD J. MOSSINGHOFF

*Attesting Officer*       *Commissioner of Patents and Trademarks*